United States Patent [19]

Klauser

[11] Patent Number: 5,044,009
[45] Date of Patent: Aug. 27, 1991

[54] SET OF X-RAY FILM HOLDERS FOR TAKING X-RAY EXPOSURES OF AN ENTIRE TOOTH

[76] Inventor: Rolf M. Klauser, Luzernerstrasse 6, CH-6010 Kriens, Switzerland

[21] Appl. No.: 520,774

[22] Filed: May 8, 1990

[30] Foreign Application Priority Data

May 10, 1989 [CH] Switzerland ............... 01757/89

[51] Int. Cl.⁵ .................. A61B 6/14; G03B 42/02
[52] U.S. Cl. ......................... 378/170; 378/168; 378/174; 378/181; 378/187; 378/205
[58] Field of Search ............. 378/170, 168, 174, 181, 378/187, 191, 205

[56] References Cited

U.S. PATENT DOCUMENTS

| | | | |
|---|---|---|---|
| Re. 25,773 | 5/1965 | Medwedeff et al. | 378/174 |
| 3,003,062 | 10/1961 | Updegrave | 378/170 |
| 3,304,422 | 2/1967 | Medwedeff et al. | 378/147 |
| 4,057,732 | 11/1977 | Klauser | 378/174 |
| 4,251,732 | 2/1981 | Fried | 378/174 |
| 4,295,050 | 10/1981 | Linden | 378/170 |
| 4,507,798 | 3/1985 | Welander | 378/170 |

FOREIGN PATENT DOCUMENTS 0279955 8/1988 European Pat. Off. .
0307617 3/1989 European Pat. Off. .

Primary Examiner—Edward P. Westin
Assistant Examiner—Don Wong
Attorney, Agent, or Firm—Ostrolenk, Faber, Gerb & Soffen

[57] ABSTRACT

The set of X-ray film holders for taking X-ray exposures of an entire tooth consists of a holder for the side teeth and a holder for the front teeth, each of the holders comprising a resilient clip for the X-ray film, a formed bite portion and a cranked indicator rod extending perpendicularly to the film plane for adjusting the central X-ray beam orthogonally to the film plane. The film clip is attached to the bite portion in such a manner that it is pivotable by 360° and may be locked in the plane which is formed by the indicator rod with its cranked portion. Except for special X-ray tubes, it is useful to have a centering aid for the central X-ray beam. To this end, an index having pointer means is movably disposed on the indicator rod, guiding means being provided on the indicator rod and on the tube of the index in order to bring the pointer means into the correct position according to whether the X-ray film is in its upward or downward position. Such a set of X-ray film holders enables exact aligning of all X-ray tubes with the currently used X-ray films for exposures of all teeth.

9 Claims, 2 Drawing Sheets

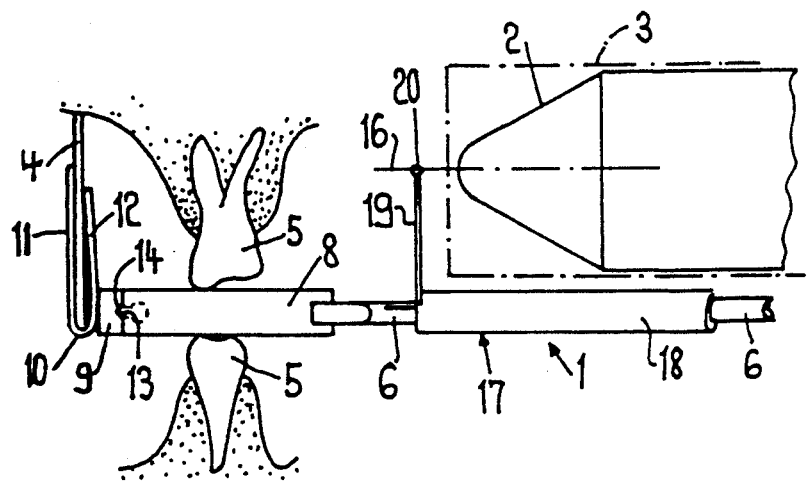
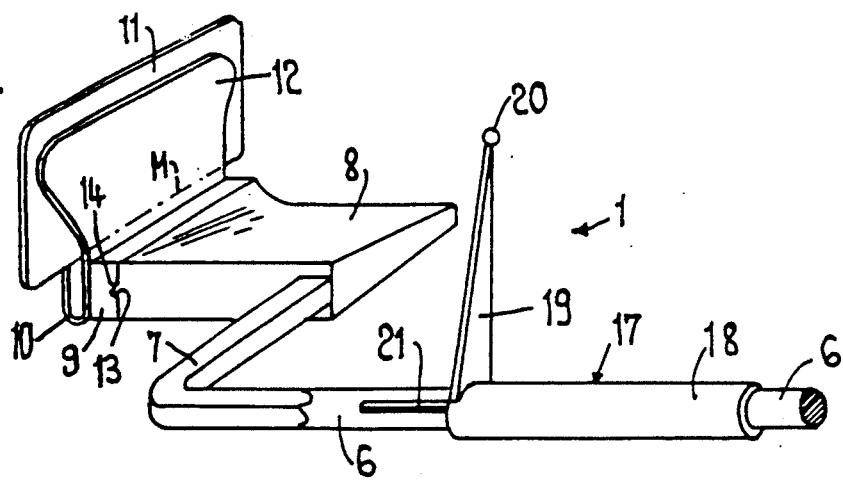
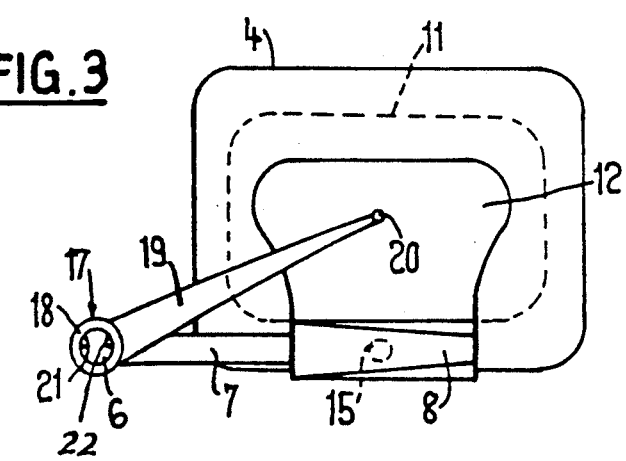
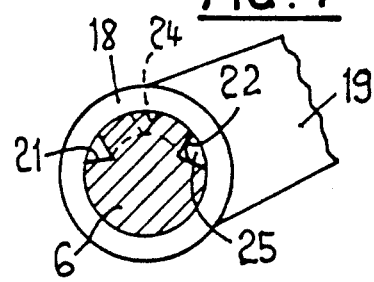
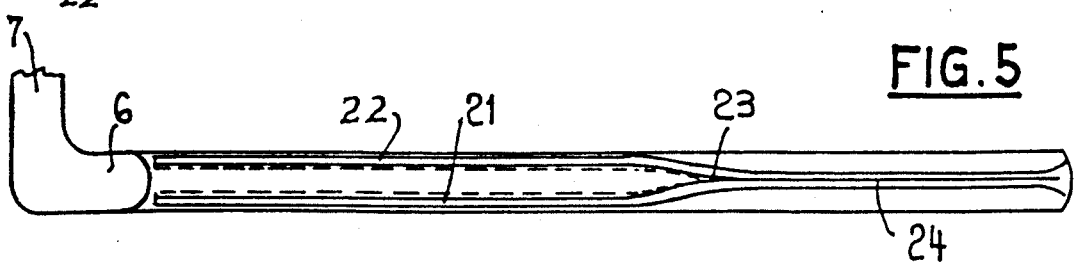

SET OF X-RAY FILM HOLDERS FOR TAKING X-RAY EXPOSURES OF AN ENTIRE TOOTH

BACKGROUND OF THE INVENTION

The present invention refers to a set of X-ray film holders for taking exposures of an entire tooth, comprising holders for apical exposure of the side teeth as well as for apical exposure of the front teeth.

In order to obtain as accurate, that is as undistorted pictures of teeth as possible, it is necessary, on one hand, to bring the X-ray film provided in a holding device into the correct position, and on the other hand, to position and adjust the X-ray tube correctly with respect to the X-ray film. A film holder having a centering device is known from U.S. Pat. No. 3,003,062, whereby all teeth can be X-rayed. This is achieved by a shank of the holder which is rotatable in its plane in order to allow exposures of either the right or the left side of the mouth, or of the lower or the upper teeth, respectively. This film holder, however, is intended for a very particular type of X-ray tubes. A pluggable member, together with a cotton pad, is used as a bite portion. Moreover, this holder has to be dissembled and reassembled for every different application.

Another holder for the exposure of all teeth is known from European Patent Application no. 078 425, this holder being assembled in a modular form from the most diverse components which have to be rearranged according to the particular needs.

SUMMARY OF THE INVENTION

By contrast, it is the object of the present invention to provide a set of X-ray film holders for taking apical X-ray pictures which guarantees an adequate guiding and centering of the central X-ray beam with all existing X-ray tubes such as short tubes and long tubes, cylindrical, conical as well as square, tapered and flat front tubes and with all intra-oral X-ray film formats; which consists of few components and is cheap in manufacture and easy to use by the dentist; and which may also be used for patients which are reclining. This object is attained by a set of X-ray film holders consisting of a holder for the side teeth and a holder for the front teeth, each of said holders comprising a resilient clip for the X-ray film, a formed bite portion and a cranked indicator rod extending perpendicularly to the film plane, for adjusting the central X-ray beam orthogonally to the film plane, and wherein said film clip is secured to said bite portion in such a manner that it is pivotable by 360° and may be locked in the plane formed by said indicator rod with its cranked portion.

The invention is now explained in more detail with reference to a drawing of embodiments.

BRIEF DESCRIPTION OF THE DRAWINGS

FIG. 1 is a side view of an X-ray film holder according to the invention for taking an exposure of side teeth, shown in the mouth of a patient;

FIG. 2 shows the holder of FIG. 1 in a perspective view;

FIG. 3 shows the holder of FIG. 2 as seen from the right;

FIG. 4 shows a detail of the holder of FIG. 3;

FIG. 5 shows a part of the holder of FIG. 3 as seen from above;

DESCRIPTION OF THE PREFERRED EMBODIMENTS

Figure 6:
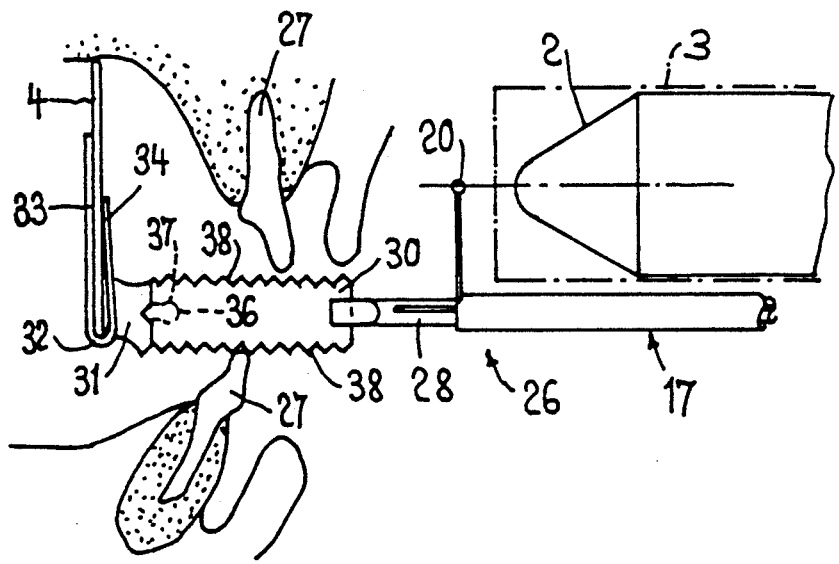
FIG. 6 is a side view of the X-ray film holder of the invention for the front teeth, shown in the mouth of a patient.

FIG. 1 shows the first X-ray film holder 1 for taking exposures of side teeth, a conical X-ray tube 2 as well as a cylindrical X-ray tube 3 illustrated by dotted lines. X-ray film holder 1 intra-orally carries X-ray film 4 which is placed behind two side teeth 5. Essential components of the X-ray film holder 1 are indicator rod 6 with its crank 7 and bite portion 8 which is again orthogonal to crank 7 and to which resilient film clip 10 is adjoined by means of a connecting piece 9 which is pivotably attached to the bite portion. Resilient film clip 10 is U-shaped and comprises a back plate 11 and a somewhat smaller clamping shank 12 which however is large enough to prevent any bending of the X-ray film. A marking M is provided on the back side of the back plate in order to center all three currently used film formats with precision. The marking is such that film formats no. 0 and no. 1 are inserted up to the marking, whereas film format no. 2 is inserted entirely. In FIG. 2 it is shown that the bite portion is not shaped as a parallel plate, but its front portion, i.e. on the side of crank 7, is thicker than the rearward portion, and its top and bottom have a slightly concavely curved configuration, both sides being roughened a little. In view of adjusting film clip 10 with respect to the bite portion, the latter is provided with a key 13, and connecting piece 9 comprises a groove 14. Of course, the disposition of these snap means might as well be reversed. Pivot axle 15, which is schematically shown in FIG. 3, may be suitably secured in the connecting piece and/or in the bite portion, e.g. by a squeezed thickening thereof.

Basically, bite-wing radiographs could be taken by means of such an X-ray film holder, provided that a determined tube type, namely a cylindrical one, is used. If different tube types are used, however, it is necessary to direct the central X-ray beam 16 (see FIG. 1) exactly onto the film center, which is the same for all three film formats. This requires an index 17 comprising a tube 18 having a perpendicularly disposed pointer 19 with an index tip 20. The length of pointer 19 is such that its tip 20 exactly corresponds to the center of all three film formats when in the precisely marked position according to the center of the film holder back plate.

As the film clip may be locked in two different positions when pivoted by 180°, i.e. in the upward or downward direction, the index, respectively its tip 20 must be adapted to point to the film center in both positions, too. To this end, indicator rod 6 is provided with two guiding channels 21 and 22 which merge into a single channel by means of a switch, this single channel 24 being disposed between said two channels, as illustrated in FIGS. 4 and 5. FIG. 4 further shows that tube 17 of the index is provided with a cam 25 which fits into the channels. Of course, this arrangement may also be reversed, i.e. the indicator rod might have two corresponding ribs and the index tube a corresponding channel. In accordance with each position of the film clip, upwards or downwards, the index may be adjusted by retracting the tube until the cam engages united channel 24, after which the tube may be inserted into the corresponding channel. In both positions, index tip 20 points exactly to the center of the back plate and hence to the center of all three film formats.

Figure 7:
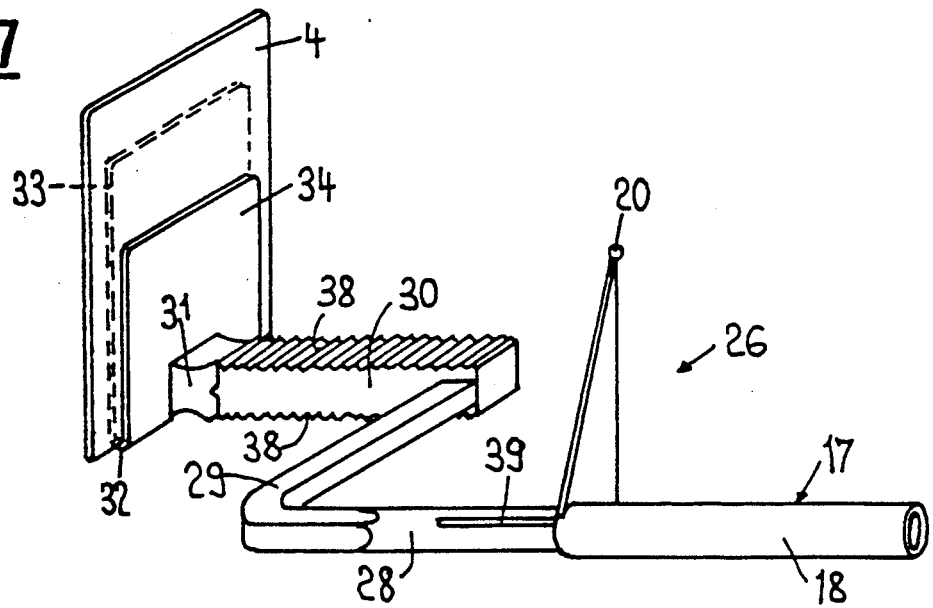
FIG. 7 shows the X-ray film holder of FIG. 6 in a perspective view.

FIGS. 6 and 7 illustrate the second X-ray film holder 26 of the set which is intended for exposures of the front teeth. Again, the two X-ray tubes 2 or 3 and the front teeth 27 are shown. This X-ray film holder also essentially consists of the indicator 28 including cranked portion 29, the adjoining bite portion 30 as well as the pivotable connecting piece 31 attached thereto. Film clip 32 is secured to connecting piece 31 and provided with a back plate 33 and a clamping shank 34. Moreover, an inserted X-ray film 4 is shown. The dimensions of back plate 33 exactly correspond to film format no. 0. All three film formats 0, 1, and 2 are inserted entirely, formats 1 and 2 somewhat projecting over the back plate on the side and at the top. The clamping shanks of both this film clip and the one of the holder for the side teeth are preferably made as thin as possible, the upper edges being internally chamfered in both cases. Of course, all corners are rounded in order to prevent any injuries. The pivotable fixture of connecting piece 31 to bite portion 30 is identical to that of the previously described holder for the side teeth and features the same key 13 and groove 14 with the fixture being effected by a thickened pin 36 in a corresponding bore 37 of the bite portion. The bite portion 30 of the holder for the front teeth has ribbed surfaces 38 on both sides, and its thickness is about constant. Index 17 of this holder for the front teeth is the same as that of the holder for the side teeth, whereas the guiding channels, of which only one, 39, is visible, enclose a different angle than in the case of the holder for the side teeth as the index tip does not point to the center of the back plate, which is the case of the holder for the side teeth, but to the center of film format no. 2 when it is inserted and exactly centered with respect to the back plate. FIGS. 2 and 7 also illustrate that indicator rods 6, and 28, respectively, have to be round while crank 7 or 29 may as well be angular.

As indicated with reference to the bite-wing holder, the principle of the guiding channel and the guiding cam in the movable index may as well be inverted, so that there may be only one guiding rib on the indicator rod, whereas the index has to be provided with two guiding channels for the two positions. As the index tips of the two holders do not include the same angle, because they point to different locations, the index of the bite-wing holder must be different from that of the holder for the front teeth if there are guiding channels in the index. In this case, it is advantageous to provide the two holders with different colorations or to identify them in any other suitable manner.

Figure 8:
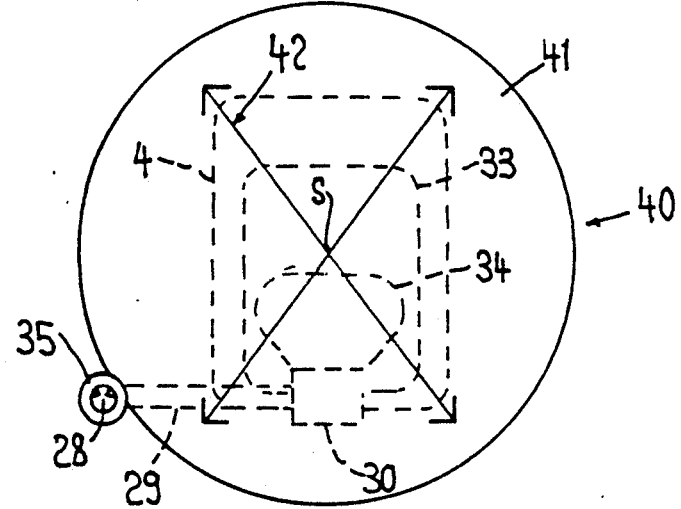
FIG. 8 shows an alternative embodiment of the preceding X-ray film holders.

The previously described index having a pointer and a pointer tip is well adapted for conical tubes, but it is a little less precise, yet sufficient, in the case of cylindrical tubes. FIG. 8 shows an alternative embodiment which is very well suited for cylindrical tubes but also for conical ones. Index 40 appears in FIG. 8, which is provided with a tube 35 and which, together with the corresponding indicator rod, has either a guiding cam or two guiding channels and is adapted, according to its use, to a holder for the side teeth or for the front teeth. Instead of an index pointer, this index features a disk 41 on which a cross 42 is drawn. Said disk is secured to tube 35 at its circumference, the circumference of the disk serving as a centering aid for cylindrical tubes while the corners of cross 42 serve as a centering aid for angulat tubes. Intersection S of the cross serves as a centering aid for conical tubes and replaces the tip of the index pointer. Further, clamping shank 32, back plate 33 and the inserted film 4 are shown by dotted lines.

All parts of these X-ray film holders are generally made from plastics in such a manner that, in particular for hygienic reasons, they are intended to be disposable or may be sterilised.

I claim:

1. A set of X-ray film holders for taking X-ray exposures of an entire tooth, including a holder for the side teeth and a holder for the front teeth, each of said holders comprising a resilient clip for an X-ray film, a bite portion and an indicator rod extending perpendicularly to the film plane, and having a crank portion connected to the bite portion, for adjusting a central X-ray beam orthogonally to the film plane, and wherein each of said film clips is pivotally secured to its bite portion in such a manner that it is pivotable by 360° in steps of 180° and may be locked in the plane formed by said indicator rod with its crank portion by snap means.

2. A set of X-ray film holders according to claim 1, wherein said holders comprise an index having a tube which is slidable on said indicator rod and to which pointer means are attached in order to serve as a reference for aligning the central X-ray beam with the center of a back plate in the case of the holder for the side teeth, or with the center of the X-ray film in the case of the holder for the front teeth, said indicator rod and said tube of said index being provided with respective means which cooperate with one another for bringing said pointer means into the respective correct upward or downward position.

3. A set of X-ray film holders according to claim 2, wherein said pointer means comprise a pointer which is attached to said tube of said index in an orthogonal position and the length of which is such that its tip serves as a reference 4. A set of X-ray film holders according to claim 2, wherein said pointer means comprise a disk having a cross drawn thereon and being attached to said tube of said index, the circumference of said disk serving as a centering aid for cylindrical X-ray tubes, the corners of said cross serving as a centering aid for rectangular X-ray tubes, and the intersection of said cross serving as a centering aid for conical tubes.

5. A set of X-ray film holders according to claim 1, wherein said bite portion of the holder for the front teeth has an approximately rectangular cross-section and ribbed surfaces on both sides.

6. A set of x-ray film holders according to claim 1, wherein the snap means between said bite portion and each of said film clips includes a connecting piece attached to each of said film clips by a key and a corresponding groove.

7. A set of X-ray film holders for taking X-ray exposures of an entire tooth, including a holder for the side teeth and a holder for the front teeth, each of said holders comprising a resilient clip for an X-ray film, a bite portion and an indicator rod extending perpendicularly to the film plane and having a crank portion connected to the bite portion, for adjusting a central X-ray beam orthogonally to the film plane, each of said film clips being pivotally secured to said bite portion in such a manner that it is pivotable by 360° in steps of 180° and may be locked in the plane formed by said indicator rod with its crank portion by snap means, said holders further comprising an index having a tube which is slidable on said indicator rod and to which pointer means are attached in order to serve as a reference for aligning the central X-ray beam with the center of a back plate in the case of the holder for the side teeth, or with the center of the X-ray film in the case of the holder for the front teeth, said indicator rod and said tube of said index being provided with respective means which cooperate with one another for bringing said pointer means into the respective correct upward or downward position, said indicator rod cooperating means comprising two guiding channels, which guiding channels merge into a single channel by means of a switch, and said tube cooperating means comprising a guiding cam which corresponds to said guiding channels, said guiding channels of said indicator rod of the holder for the side teeth enclosing a different angle of aperture than those of the holder for the front teeth.

8. A set of X-ray film holders for taking X-ray exposures of an entire tooth, including a holder for the side teeth and a holder for the front teeth, each of said holders comprising a resilient clip for an X-ray film, a bite portion and an indicator rod extending perpendicularly to the film plane and having a crank portion connected to the bite portion, for adjusting a central X-ray beam orthogonally to the film plane, each of said film clips being pivotally secured to said bite portion in such a manner that it is pivotable by 360° in steps of 180° and may be locked in the plane formed by said indicator rod with its crank portion by snap means, said holders further comprising an index having a tube which is slidable on said indicator rod and to which pointer means are attached in order to serve as a reference for aligning the central X-ray beam with the center of a back plate in the case of the holder for the side teeth, or with the center of the X-ray film in the case of the holder for the front teeth, said indicator rod and said tube of said index being provided with respective means which cooperate with one another for bringing said pointer means into the respective correct upward or downward position, said indicator rod cooperating means comprising a guiding cam on said indicator rod and said tube cooperating means comprising two guiding channels, the guiding channels of said tube for one of said holders enclosing a different angle of aperture than those of said tube for the other of said holder.

9. A set of X-ray film holders for taking X-ray exposures of an entire tooth, including a holder for the side teeth and a holder for the front teeth, each of said holders comprising a resilient clip for an X-ray film, a bite portion and an indicator rod extending perpendicularly to the film plane and having a crank portion connected to the bite portion, for adjusting a central X-ray beam orthogonally to the film plane, each of said film clips pivotally secured to said bite portion in such a manner that it is pivotable by 360° in steps of 180° and may be locked in the plane formed by said indicator rod with its crank portion by snap means, and the thickness of said bite portion of the holder for the side teeth being thicker on the side of the crank of said indicator rod than on the other side, both sides of said bite portion being slightly concavely curved and roughened.

* * * * *